(12) United States Patent
Ohkubo et al.

(10) Patent No.: US 8,552,239 B2
(45) Date of Patent: Oct. 8, 2013

(54) OLEFIN PRODUCTION PROCESS

(75) Inventors: Tsuneyuki Ohkubo, Ichihara (JP);
Kenji Fujiwara, Kamakura (JP);
Terunori Fujita, Yokohama (KR);
Masayasu Ishibashi, Iwakuni (JP)

(73) Assignee: Mitsui Chemicals, Inc., Tokyo (JP)

( * ) Notice: Subject to any disclaimer, the term of this patent is extended or adjusted under 35 U.S.C. 154(b) by 28 days.

(21) Appl. No.: 13/255,239

(22) PCT Filed: Mar. 12, 2010

(86) PCT No.: PCT/JP2010/054169
§ 371 (c)(1),
(2), (4) Date: Sep. 7, 2011

(87) PCT Pub. No.: WO2010/106966
PCT Pub. Date: Sep. 23, 2010

(65) Prior Publication Data
US 2012/0010453 A1    Jan. 12, 2012

(30) Foreign Application Priority Data

Mar. 16, 2009   (JP) .................................. 2009-062686

(51) Int. Cl.
*C07C 1/20* (2006.01)

(52) U.S. Cl.
USPC ............................. 585/638; 502/347; 502/348

(58) Field of Classification Search
USPC ......... 585/638, 639, 640, 641, 642, 422, 446;
568/798, 799, 768, 385, 565, 569, 577,
568/741; 502/60–71
See application file for complete search history.

(56) References Cited

U.S. PATENT DOCUMENTS

| | | | |
|---|---|---|---|
| 4,554,260 A | | 11/1985 | Pieters et al. |
| 5,017,729 A | * | 5/1991 | Fukuhara et al. ............. 568/798 |
| 6,046,373 A | * | 4/2000 | Sun .............................. 585/640 |
| 6,888,035 B2 | | 5/2005 | Fallon et al. |
| 7,405,337 B2 | | 7/2008 | Kalnes et al. |
| 2004/0116749 A1 | * | 6/2004 | Levin et al. ................... 568/385 |
| 2010/0311135 A1 | | 12/2010 | Takebayashi et al. |

FOREIGN PATENT DOCUMENTS

| | | |
|---|---|---|
| CN | 1043956 A | 7/1990 |
| DE | 84378 | 9/1971 |
| EP | 1 974 812 A1 | 10/2008 |
| JP | 61-067493 | 4/1986 |
| JP | 02-174737 | 7/1990 |
| JP | 03-041035 | 2/1991 |
| JP | 03-041038 | 2/1991 |
| JP | 06-091171 | 4/1994 |
| JP | 2008-513449 | 5/2008 |
| WO | WO 02/066407 A1 | 8/2002 |
| WO | WO-2009/008377 A1 | 1/2009 |

OTHER PUBLICATIONS

Vazquez et al. "Silica Supported Heteropolyacids as Catalysts in Alcohol Dehydration Reactions." Journal of Molecular Catalysis A: Chemical 161 (2000) 223-232.*
Bermejo, Lourdes L. et al., "Expression of Clostridium acetobutylicum ATCC 824 Genes in *Escherichia coli* for Acetone Production and Acetate Detoxification," Applied and Environmental Microbiology, Mar. 1998, vol. 64, No. 3, pp. 1079-1085.
International Search Report mailed Jun. 22, 2010 in International Application No. PCT/JP2010/054169.
Russian Office Action for Application No. 2011126629/(039472), dated Feb. 8, 2012 with English translation.
Written Opinion and Search Report Singapore Application No. 201103938-5 dated Jul. 12, 2012.
Non-Final Office Action U.S. Appl. No. 13/131,905 dated Dec. 7, 2012.

* cited by examiner

*Primary Examiner* — In Suk Bullock
*Assistant Examiner* — Sharon Pregler
(74) *Attorney, Agent, or Firm* — Foley & Lardner LLP

(57) ABSTRACT

A novel olefin production process is provided which can be established as an industrial and practical process capable of producing olefins by directly reacting a ketone and hydrogen in a single reaction step. In particular, a novel olefin production process is provided in which propylene is obtained with high selectivity by directly reacting acetone and hydrogen.
The olefin production process according to the present invention includes reacting a ketone and hydrogen in the presence of at least one dehydration catalyst and a silver-containing catalyst, and the at least one dehydration catalyst is selected from metal oxide catalysts containing a Group 6 element, zeolites, aluminas and heteropoly acid salts in which part or all the protons in heteropoly acids are exchanged with metal cations.

8 Claims, No Drawings

OLEFIN PRODUCTION PROCESS

TECHNICAL FIELD

The present invention relates to processes for producing olefins by reacting a ketone and hydrogen. In more detail, the invention relates to processes for producing olefins with high selectivity from a ketone and hydrogen as starting materials in a single reaction step.

In particular, the invention is concerned with processes for producing propylene by reacting acetone and hydrogen. In more detail, the invention pertains to processes for producing propylene from acetone and hydrogen as starting materials in a single reaction step.

BACKGROUND ART

A reaction between benzene and propylene gives cumene. Oxidation of cumene results in cumene hydroperoxide. The cumene hydroperoxide is acid decomposed into phenol and acetone. A combination of these known reactions is the cumene process which is currently a mainstream process for the production of phenol.

The cumene process gives acetone as a by-product, and is valuable when both phenol and acetone are required. However, if the acetone produced is in excess of demand, the economic efficiency is deteriorated due to the price difference between acetone and starting material propylene. Methods have been then proposed in which by-product acetone is reused as a material in the cumene process through various reactions.

Acetone is readily hydrogenated to isopropanol. Patent Document 1 discloses a process in which the isopropanol thus obtained is dehydrated to propylene and the propylene is reacted with benzene to give cumene, in detail acetone is reused as a material in the cumene process by being converted to propylene through two reaction steps.

In the reuse of acetone, an industrial and practical process should be established which is capable of producing propylene from acetone with high selectivity. Further, the establishment of industrial and practical processes capable of producing not only propylene but other olefins from general ketones with high selectivity is also valuable in other various processes.

Patent Document 2 discloses a process in which propylene is obtained through hydrogenation of acetone at 400° C. in the presence of a catalyst containing Cu (25%), zinc monoxide (35%) and aluminum monoxide (40%). In spite of the high reaction temperature of 400° C., however, the acetone conversion is low at 89%. Further, the propylene selectivity according to this document is only 89% because of a side reaction hydrogenating propylene to propane.

CITATION LIST

Patent Literatures

Patent Document 1: JP-A-H02-174737
Patent Document 2: East German Patent DD84378

SUMMARY OF INVENTION

Technical Problem

It is therefore an object of the present invention to provide a novel olefin production process that can be established as an industrial and practical process capable of producing olefins with high selectivity by directly reacting a ketone and hydrogen in a single reaction step. In particular, an object of the invention is to provide a novel propylene production process in which propylene is obtained with high selectivity by directly reacting acetone and hydrogen.

Solution to Problem

The present inventors studied diligently to achieve the above objects. They have then found that olefins are produced with high selectivity by reacting a ketone and hydrogen in a single reaction step in the presence of a specific dehydration catalyst and a silver-containing catalyst.

In particular, it has been found that propylene can be produced in high yield from acetone and hydrogen as starting materials.

An olefin production process according to the present invention comprises reacting a ketone and hydrogen in the presence of at least one dehydration catalyst and a silver-containing catalyst, the at least one dehydration catalyst being selected from metal oxide catalysts containing at least one Group 6 (VIB) element, zeolites, aluminas and heteropoly acid salts in which part or all the protons in heteropoly acids are exchanged with metal cations.

In a preferred embodiment, the silver-containing catalyst further contains at least one Group 13 (IIIA) element.

The dehydration catalyst is preferably at least one dehydration catalyst selected from zeolites, γ-aluminas, tungsten oxide, molybdenum oxide and heteropoly acid salts in which part or all the protons in heteropoly acids are exchanged with metal cations.

In a preferred embodiment, the ketone is acetone and the olefin is propylene.

The heteropoly acid is preferably at least one heteropoly acid selected from phosphotungstic acid, silicotungstic acid, phosphomolybdic acid and silicomolybdic acid.

The heteropoly acid salt is preferably supported on silica.

The reaction temperature in the reaction is preferably in the range of 50 to 500° C.

The reaction is preferably catalyzed by a mixture of the dehydration catalyst and the silver-containing catalyst.

The ketone is preferably acetone obtained with an isopropyl alcohol-producing bacterium that produces isopropyl alcohol and acetone from a plant-derived material, and the olefin is preferably propylene.

Advantageous Effects of the Invention

According to the processes of the invention, olefins can be produced from a ketone and hydrogen as starting materials in a single reaction step with industrial and practical advantages. In particular, the novel propylene production processes of the invention can produce propylene with high selectivity by directly reacting acetone and hydrogen.

DESCRIPTION OF EMBODIMENTS

In an olefin production process according to the present invention, a ketone and hydrogen are reacted in the presence of at least one dehydration catalyst and a silver-containing catalyst. The at least one dehydration catalyst is selected from metal oxide catalysts containing at least one Group 6 (VIB) element, zeolites, aluminas and heteropoly acid salts in which part or all the protons in heteropoly acids are exchanged with metal cations.

In the present invention, two components are used as catalysts, namely, a silver-containing catalyst and at least one dehydration catalyst selected from metal oxide catalysts containing at least one Group 6 (VIE) element, zeolites, aluminas and heteropoly acid salts in which part or all the protons in heteropoly acids are exchanged with metal cations. The catalyst components may be used in any manner without limitation. In an embodiment, the dehydration catalyst and the silver-containing catalyst may be physically mixed on a catalyst particle level with a centimeter size. In another embodiment, the catalysts may be finely pulverized and mixed together, and the mixture may be shaped into catalyst particles with a centimeter size. In a still another embodiment, the dehydration catalyst may be used as a carrier, and the silver-containing catalyst may be supported thereon. Alternatively, the dehydration catalyst may be supported on the silver-containing catalyst as a carrier.

In the olefin production processes according to the invention, it is considered that the silver-containing catalyst catalyzes hydrogenation of the ketone into an alcohol and the dehydration catalyst catalyzes dehydration of the alcohol to an olefin. When the ketone is acetone for example, reactions are considered to take place such that acetone is hydrogenated into isopropyl alcohol under the catalysis of the silver-containing catalyst and the isopropyl alcohol is dehydrated by the dehydration catalyst to give propylene and water.

That is, it is considered that the hydrogenation reaction and the dehydration reaction take place stepwise in the olefin production processes of the invention. Accordingly, the catalysts may form distinct catalyst layers in the appropriate order suited for the reactions, or the silver-containing catalyst and the dehydration catalyst may be mixed in a graded mixing ratio.

The ketones used in the invention may be selected appropriately depending on the target olefins. For example, acetone is used to produce propylene, and methyl ethyl ketone is used to obtain 1-butene.

The olefin production processes of the invention are suited for the production of propylene from acetone.

The ketones may be obtained by any methods without limitation. For example, acetone that is by-produced in the production of phenol, and methyl ethyl ketone from dehydrogenation of 2-butanol may be used. When the ketone is acetone, acetone may be used which is obtained with an isopropyl alcohol-producing bacterium that produces isopropyl alcohol and acetone from a plant-derived material.

The plant-derived materials are not particularly limited as long as they are carbon sources obtained from plants and are metabolized to isopropyl alcohol by bacteria. The plant-derived materials include organs such as roots, stems, trunks, branches, leaves, flowers and seeds, plants or plant organs having these organs, and degradation products of these plant-derived materials. Further, the term plant-derived materials in the invention includes carbon sources obtained from plants, plant organs or degradation products thereof that can be used as carbon sources by bacteria in culture. Examples of the carbon sources as the plant-derived materials include sugars such as starch, glucose, fructose, sucrose, xylose and arabinose, and plant degradation products and cellulose hydrolysates containing large amounts of the above sugars. Further, the carbon sources in the invention include plant oil-derived glycerols and fatty acids. Preferred plant-derived materials include agricultural crops such as grain, and corn, rice, wheat, bean, sugarcane, beet and cotton. These materials may be used in any form without limitation, and for example may be used in the form of unprocessed product, squeezed juice or milled product. In an embodiment, the carbon sources as described above may be used directly.

The isopropyl alcohol-producing bacteria are not limited as long as they can produce isopropyl alcohol and acetone from the plant-derived materials. For example, there may be used bacteria that are cultured on the plant-derived materials and secrete isopropyl alcohol and acetone in the culture medium after a given time. Such isopropyl alcohol-producing bacteria are described in literature such as WO 2009/008377, Chinese Patent Application No. CN1043956A, JP-A-S61-67493, and Applied and Environmental Microbiology, Vol. 64, No. 3, pp. 1079-1085 (1998). In particular, isopropyl alcohol-producing bacteria described in WO 2009/008377 are preferred.

The isopropyl alcohol-producing bacteria described in WO 2009/008377 are given acetoacetic acid decarboxylase activity, isopropyl alcohol dehydrogenase activity, CoA transferase activity and thiolase activity.

The words the bacteria are "given" the activities mean that an enzyme-encoding gene is introduced into the host bacteria from outside the bacteria, and that an enzyme gene possessed by the host bacteria on the genome is strongly expressed by enhancing the promoter activity or replacing the promoter with another promoter.

In a preferred embodiment, the acetoacetic acid decarboxylase activity, the isopropyl alcohol dehydrogenase activity, the CoA transferase activity and the thiolase activity are obtained by the introduction of a gene that encodes an enzyme derived from at least one selected from the group consisting of *Clostridium* bacteria, *Bacillus* bacteria and *Escherichia* bacteria.

In a more preferred embodiment, the acetoacetic acid decarboxylase activity and the isopropyl alcohol dehydrogenase activity are obtained by the introduction of a gene that encodes an enzyme derived from *Clostridium* bacteria, and the CoA transferase activity and the thiolase activity are obtained by the introduction of a gene that encodes an enzyme derived from *Escherichia* bacteria.

In a particularly preferred embodiment, the acetoacetic acid decarboxylase activity is obtained by the introduction of a gene that encodes an enzyme derived from *Clostridium acetobutylicum*, the isopropyl alcohol dehydrogenase activity is obtained by the introduction of a gene that encodes an enzyme derived from *Clostridium beijerinckii,* and the CoA transferase activity and the thiolase activity are obtained by the introduction of a gene that encodes an enzyme derived from *Escherichia coli.*

In another preferred embodiment, the acetoacetic acid decarboxylase activity, the isopropyl alcohol dehydrogenase activity, the CoA transferase activity and the thiolase activity are each obtained by the introduction of a gene that encodes an enzyme derived from *Clostridium* bacteria.

The isopropyl alcohol-producing bacteria are preferably *Escherichia coli.*

The production of isopropyl alcohol and acetone from the plant-derived materials by the isopropyl alcohol-producing bacteria usually gives by-products such as water and carboxylic acids. When acetone obtained from the plant-derived material with the isopropyl alcohol-producing bacteria is used as the ketone in the invention, the acetone may be purified to high purity by removing the isopropyl alcohol, water and other by-products from the product.

Alternatively, the isopropyl alcohol and acetone in the product may be concentrated to a high concentration while the by-products are removed. When such acetone is used in the process of the invention, the isopropyl alcohol and water will be supplied to a reactor together with the acetone. The isopropyl alcohol is dehydrated by the dehydration catalyst, producing propylene and water.

The hydrogen reacted with the ketone in the invention may be a molecular hydrogen gas or a hydrocarbon such as cyclohexane that generates hydrogen when subjected to reaction conditions. Theoretically, the hydrogen may be used at least in an equimolar amount relative to the ketone. From the viewpoint of separation and recovery, the hydrogen may be preferably used in an equimolar to thirty-fold molar amount, and more preferably in an equimolar to fifteen-fold molar amount relative to the ketone. When the ketone conversion is desired to be less than 100%, the hydrogen amount may be controlled less than the equimolar amount relative to the ketone. In the invention, the hydrogen reacts with the oxygen atom in the ketone to form water, and the water produced may be recovered from a reactor outlet. An excess of hydrogen over the ketone is not substantially consumed as long as undesirable side reactions do not take place.

The hydrogen gas is generally supplied to a reactor continuously, but the supply methods are not particularly limited thereto. In an embodiment, the hydrogen gas may be supplied intermittently such that the hydrogen is supplied at the initiation of the reaction and the supply is suspended during the reaction and restarted after a prescribed time. In the case of a liquid-phase reaction, the hydrogen gas may be supplied while being dissolved in a solvent. In a recycle process, hydrogen gas recovered from the column top together with low-boiling fractions may be resupplied. The pressure of the hydrogen supplied is generally equal to the pressure in the reactor, but may be appropriately adjusted depending on the hydrogen supply methods.

In the invention, the reaction may be carried out by any methods under any conditions without limitation. Exemplary conditions and methods are described below.

The contact between the starting materials, i.e., the ketone and the hydrogen gas, may take place in a gas-liquid countercurrent flow or a gas-liquid co-current flow. The liquid and gas directions may be descending liquid/ascending gas, ascending liquid/descending gas, ascending liquid/ascending gas, or descending liquid/descending gas.

<Dehydration Catalysts>

In the invention, at least one dehydration catalyst is used which is selected from metal oxide catalysts containing at least one Group 6 (VIB) element, zeolites, aluminas and heteropoly acid salts in which part or all the protons in heteropoly acids are exchanged with metal cations. The dehydration catalysts may be used singly, or two or more kinds may be used in combination.

The metal oxide catalysts containing at least one Group 6 (VIB) element include tungsten oxide and molybdenum oxide.

The zeolites that are inorganic crystalline porous compounds mainly composed of silicon and aluminum are suitable dehydration catalysts from the viewpoints of heat resistance and acid strength. Suitable zeolites may be selected appropriately depending on the molecular diameter of the alcohols which are considered as intermediates in the invention and the target olefins.

In detail, zeolites having an eight to sixteen-membered oxygen ring pore are preferably used.

Examples of the zeolites having an eight to sixteen-membered oxygen ring pore include chabazite, erionite, ferrierite, heulandite, ZSM-5, ZSM-11, ZSM-12, NU-87, theta-1, weinbergerite, X-type zeolite, Y-type zeolite, USY-type zeolite, mordenite, dealuminated mordenite, f3-zeolite, MCM-22, MCM-36, MCM-56, gmelinite, offretite, cloverite, VPI-5 and UTD-1.

Of the zeolites, those having a pore size approximately the same as the molecular diameter of the alcohols are preferable, and zeolites having an eight to twelve-membered oxygen ring pore are more preferable. Examples of the zeolites having an eight to twelve-membered oxygen ring pore include chabazite, erionite, Y-type zeolite, USY-type zeolite, mordenite, dealuminated mordenite, β-zeolite, MCM-22, MCM-56, ZSM-12 and ZSM-5. In the zeolites, the composition ratio between silicon and aluminum (silicon/aluminum) is in the range of 2/1 to 200/1, and in view of activity and heat stability, preferably in the range of 5/1 to 100/1. Further, isomorphously substituted zeolites may be used in which aluminum atoms in the zeolite skeleton are substituted with other metal such as Ga, Ti, Fe, Mn or B.

Examples of the aluminas include α-alumina and γ-alumina. In particular, γ-alumina is preferably used from the viewpoints of heat resistance and acid strength of the dehydration catalyst.

In the heteropoly acid salts used in the invention, part or all the protons in heteropoly acids are exchanged with metal cations, namely, at least part of the protons in heteropoly acids are exchanged with metal cations. In a preferred embodiment, at least one heteropoly acid is selected from phosphotungstic acid, silicotungstic acid, phosphomolybdic acid and silicomolybdic acid. These preferred heteropoly acids are obtainable in the industry. Preferred metal cations are alkali metal cations and alkaline earth metal cations. The alkali metal cations are more preferable, and potassium cation and cesium cation are particularly preferable.

Examples of the heteropoly acid salts include potassium phosphotungstate, potassium silicotungstate, potassium phosphomolybdate, potassium silicomolybdate, cesium phosphotungstate, cesium silicotungstate, cesium phosphomolybdate and cesium silicomolybdate. In these salts, at least part of the protons should be exchanged with the metal cations, and all the protons may be exchanged with the metal cations.

The heteropoly acid salt may be supported on a carrier. Examples of the carriers include silica, alumina, titania, zirconia, silica-alumina, silica-titania and silica-zirconia, with silica being particularly preferable. In a preferred embodiment, the heteropoly acid salt is supported on silica. The heteropoly acid salt may be supported on the carrier by known methods, for example by a method described in JP-A-H06-91171.

In a preferred embodiment, at least one dehydration catalyst is selected from the zeolites, γ-alumina, tungsten oxide, molybdenum oxide and heteropoly acid salts in which part or all the protons in heteropoly acids are exchanged with metal cations. The heteropoly acid salts are most preferable because undesired side reactions such as aldol condensation of ketone, olefin oligomerization and olefin hydrogenation are inhibited.

The shape of the dehydration catalysts is not particularly limited, and the dehydration catalysts may be in the form of sphere, cylindrical column, extrudate or crushed particles. The size of the particles of the dehydration catalysts may be selected in the range of 0.01 mm to 100 mm depending on the size of a reactor. When the dehydration catalyst is supported on the carrier, the particle size of the supported catalyst is preferably in the above range.

The dehydration catalysts may be used singly, or two or more kinds may be used in combination.

Silver-Containing Catalysts

The silver-containing catalysts in the invention are not particularly limited as long as the catalysts contain silver element and function as hydrogenation catalysts.

The silver-containing catalysts may be used singly, or two or more kinds may be used in combination.

The silver-containing catalysts catalyze the hydrogenation of ketones but substantially do not function as hydrogenation catalysts for olefins. Accordingly, paraffins that are by-produced by hydrogenation of olefins may be reduced compared to reactions catalyzed by, for example, copper-containing hydrogenation catalysts. In the case where the ketone is acetone, the production of by-product propane may be suppressed by the use of the silver-containing catalyst.

In a preferred embodiment, the silver-containing catalysts further contain at least one Group 13 (IIIA) element. The Group 13 (IIIA) elements include aluminum and indium. In particular, the silver-containing catalyst which further contains indium does not induce the hydrogenation of the target olefins and thereby can reduce the by-production of paraffins more effectively.

Examples of the silver-containing catalysts include $Ag_2O$ (metal oxide), AgCl (metal chloride) and metal cluster compounds such as Cu—Ag.

The silver-containing catalyst may be supported on a carrier. Examples of the carriers include silica, alumina, silica alumina, titania, magnesia, silica magnesia, zirconia, zinc oxide, carbon, acid clay, diatomaceous earth and zeolite. In a preferred embodiment, at least one carrier is selected from silica, alumina, silica alumina, titania, magnesia, silica magnesia, zirconia, zinc oxide and carbon.

The silver-containing catalyst may be supported on the carrier by soaking the carrier in an aqueous solution of silver nitrate or the like and calcining the carrier. Alternatively, silver may be bonded with an organic molecule ligand to become soluble in organic solvents, and the carrier may be soaked in a solution of the silver-ligand complex in an organic solvent and thereafter calcined. Taking advantage of the characteristic that some of the complexes are vaporized under vacuum, such complexes may be supported on the carrier by deposition or the like. Further, a coprecipitation method may be adopted in which the carrier is obtained from a corresponding metal salt in the presence of silver which will form the hydrogenation catalyst and thereby the carrier synthesis and the supporting of the silver-containing catalyst are carried out simultaneously.

Commercially available silver-containing catalysts include Ag-supporting silica catalysts and Ag-supporting alumina catalysts. The silver-containing catalysts maybe used singly, or two or more kinds may be used in combination.

The silver-containing catalysts which further contain at least one Group 13 (IIIA) element may be prepared by, for example, supporting a Group 13 (IIIA) element on the silver-containing catalyst.

The silver-containing catalysts may achieve higher activity or selectivity by the addition thereto of metal salts such as $PbSO_4$, $FeCl_2$ and $SnCl_2$, alkali metals such as K and Na, alkali metal salts, or $BaSO_4$. Such metal components may be added as required.

The shape of the silver-containing catalysts is not particularly limited, and the silver-containing catalysts may be in the form of sphere, cylindrical column, extrudate or crushed particles. The size of the particles of the silver-containing catalysts may be selected in the range of 0.01 mm to 100 mm depending on the size of a reactor.

As described hereinabove, the silver-containing catalyst maybe supported on the dehydration catalyst. For example, the silver-containing catalyst supported on the dehydration catalyst may be prepared by soaking the dehydration catalyst in an aqueous solution of silver nitrate or the like and calcining the dehydration catalyst. Alternatively, silver may be bonded with an organic molecule ligand to become soluble in organic solvents, and the dehydration catalyst may be soaked in a solution of the silver-ligand complex in an organic solvent and thereafter calcined. Taking advantage of the characteristic that some of the complexes are vaporized under vacuum, such complexes may be supported on the dehydration catalyst by deposition or the like. Further, a coprecipitation method may be adopted in which the dehydration catalyst is obtained from a corresponding metal salt in the presence of silver which will form the silver-containing catalyst and thereby the carrier synthesis and the supporting of the silver-containing catalyst are carried out simultaneously.

The reaction temperature in the invention is not particularly limited, but is preferably in the range of 50 to 500° C., and more preferably 60 to 400° C. The reaction pressure is preferably in the range of 0.1 to 500 atm, and more preferably 0.5 to 100 atm.

The amount of the catalysts is not particularly limited in the invention. In an embodiment in which the reaction is performed in a fixed bed flow apparatus, the catalyst amount may be such that the supply amount (weight) of the starting material (ketone) per hour divided by the catalyst weight (the total weight of the silver-containing catalyst and the dehydration catalyst), namely, the weight hourly space velocity (WHSV) is preferably in the range of 0.01 to 200 /h, and more preferably 0.02 to 100 /h.

The weight ratio of the dehydration catalyst and the silver-containing catalyst is not particularly limited, but the dehydration catalyst:silver-containing catalyst (weight ratio) is usually in the range of 1:0.01 to 1:100, and preferably 1:0.05 to 1:50. An excessively small weight ratio of the dehydration catalyst results in insufficient dehydration reaction and low yield of olefins, causing economic disadvantages. An excessively large weight ratio of the dehydration catalyst can be uneconomical because the ketone conversion is lowered.

In the case where the reaction is performed in a fixed bed reactor, the packing mode of the dehydration catalyst and the silver-containing catalyst may greatly affect the reaction results. As described hereinabove, the hydrogenation reaction and the dehydration reaction probably take place stepwise in the invention. Accordingly, the catalysts are preferably packed in the appropriate order suited for the reactions in order to catalyze the reactions effectively and prevent undesired side-reactions.

In particular, increasing the hydrogen pressure or the reaction temperature to accelerate the reaction rate usually involves undesired side-reactions that are not observed at low hydrogen pressure or low reaction temperature. In such cases, the reaction results can be greatly influenced by the catalyst packing manner.

For example, the catalysts may be packed in the appropriate order suited for the reactions in a manner such that: (1) the dehydration catalyst and the silver-containing catalyst are mixed together and the mixture is packed in the reactor; (2) the silver-containing catalyst forms a layer (on the upstream side) and the dehydration catalyst forms a layer (on the downstream side); (3) the dehydration catalyst supporting the silver-containing catalyst is packed in the reactor; (4) the silver-containing catalyst forms a layer (on the upstream side), and the dehydration catalyst and the silver-containing catalyst together form a layer (on the downstream side); (5) the silver-containing catalyst forms a layer (on the upstream side), and the dehydration catalyst supporting the silver-containing catalyst forms a layer (on the downstream side); (6) the dehydration catalyst and the silver-containing catalyst together form a layer (on the upstream side) and the dehydration catalyst forms a layer (on the downstream side); or (7) the dehydration catalyst supporting the silver-containing catalyst forms a layer (on the upstream side) and the dehydration catalyst forms a layer (on the downstream side). Here, the term upstream side means an inlet side of the reactor, in other words, this term indicates that the starting materials are passed through the layer in the first half of the reaction. The term downstream side means an outlet side of the reactor, in other words, this term indicates that the materials are passed through the layer in the last half of the reaction. In an embodiment of the reaction in which the ketone and hydrogen are contacted in a gas-liquid countercurrent flow, the inlet side of the reactor indicates an inlet for introducing the ketone.

In an embodiment for carrying out the invention, the reaction may be carried out in a diluted reaction system by supplying a solvent or a gas that is inert to the catalysts and the reaction materials.

The reaction may be performed by a batch process, a semi-batch process or a continuous flow process. The reaction phase may be a liquid phase, a gas phase or a gas-liquid mixed phase. The catalyst packing modes include fixed bed systems, fluidized bed systems, suspended bed systems and multistage fixed bed systems.

In the invention, the dehydration catalyst and the silver-containing catalyst may be dehydrated by known methods.

In the case of fixed bed reaction system, the dehydration catalyst and the silver-containing catalyst may be dehydrated by being held at a temperature of 300° C. or above for at least 10 minutes while passing an inert gas such as nitrogen or helium through the reactor packed with the catalysts. To develop the activity of the silver-containing catalyst, the dehydration treatment may be followed by a treatment under a stream of hydrogen.

In the event that the catalyst activity is lowered after a time of reaction, the dehydration catalyst and the silver-containing catalyst may be regenerated by known methods to recover the activity.

To maintain the yield of olefins, two or three reactors may be arranged in parallel to adopt a merry-go-round system in which the catalysts in one reactor are regenerated while the reaction is continuously carried out in the remaining one or two reactors. When the process involves three reactors, two of these reactors may be connected in series to stabilize the production output. When the reaction is carried out in a fluidized bed flow reaction system or in a moving bed reaction system, part or the whole of the catalysts may be withdrawn from the reactor continuously or intermittently while a corresponding amount of the catalysts is newly added to maintain the activity at a constant level.

EXAMPLES

The present invention will be described in greater detail by presenting examples without limiting the scope of the invention.

Production Example 1

A 300 ml pear shaped flask was charged with 50.0 g of silica gel (Wakogel C-100, manufactured by Wako Pure Chemical Industries, Ltd.), 4.77 g of silver lactate (0.5 hydrate) and 100 ml of ion exchange water. These materials were mixed together using a rotary evaporator at room temperature for 1 hour. Water was distilled away at a reduced pressure of 20 mm Hg at 40 to 50° C. Thus, silver was supported on the silica gel. The silver-supporting silica gel was subjected to reduction treatment in which the temperature was increased stepwise from 100° C. to 300° C. in 5 hours under a stream of hydrogen. As a result, 52.5 g of black 5% Ag/silica catalyst was obtained. The 5% Ag/silica catalyst was sieved to 250 to 500 µm.

Example 1

A fixed bed reaction apparatus was used which was equipped with a high-pressure feed pump, a high-pressure hydrogen mass flow controller, a high-pressure nitrogen mass flow controller, an electric furnace, a reactor having a catalyst-packing part, and a back pressure valve. A pressurized liquid-phase downflow reaction was carried out in the reaction apparatus.

The reactor was a SUS 316 reactor having an inner diameter of 1 cm. The 5% Ag/silica catalyst (classified to 250 to 500 µm) from Production Example 1 in an amount of 6.0 g was mixed with 0.6 g'of β-zeolite (manufactured by JGC Catalysts and Chemicals Ltd., compacted at 20 MPa and classified to 250 to 500 µm). The mixture was packed in the reactor from the outlet side to form a catalyst layer.

The pressure was increased to 3.0 MPa with hydrogen. Under a stream of hydrogen at 12 ml/min, acetone was passed from the inlet side of the reactor at a rate of 0.30 g/h at 180° C.

Nitrogen was introduced at 50 ml/min in the middle between the reactor outlet and the back pressure valve through the high-pressure nitrogen mass flow controller. GC (a gas chromatograph) was located in the line downstream from the back pressure valve, and the reaction products were quantitatively determined online. The reaction results are set forth in Table 1. Propylene was produced with good selectivity as shown in Table 1.

Production Example 2

A 300 ml pear shaped flask was charged with 29.1 g of the 5% Ag/silica catalyst from Production Example 1, 0.43 g of indium nitrate trihydrate and 100 ml of ion exchange water. These materials were mixed together using a rotary evaporator at room temperature for 1 hour. Water was distilled away at a reduced pressure of 20 mm Hg at 40 to 50° C. Thus, indium nitrate was supported on the 5% Ag/silica catalyst. The indium-supporting 5% Ag/silica catalyst was subjected to reduction treatment in which the temperature was increased stepwise from 100° C. to 300° C. in 3 hours under a stream of hydrogen. As a result, 29.2 g of black 5% Ag-0.5% In/silica catalyst was obtained. The 5% Ag-0.5% In/silica catalyst was sieved to 250 to 500 µm.

Example 2

Reaction was performed in the same manner as in Example 1, except that the 5% Ag/silica catalyst was replaced by the 5% Ag-0.5% In/silica catalyst from Production Example 2, and the hydrogen flow rate was increased from 12 ml/min to 22 ml/min.

The reaction results are set forth in Table 1. Propylene was produced with good selectivity as shown in Table 1.

Example 3

Reaction was performed in the same manner as in Example 2, except that the reaction temperature was increased from 180° C. to 240° C.

The reaction results are set forth in Table 1. Propylene was produced with good selectivity as shown in Table 1.

Example 4

Reaction was performed in the same manner as in Example 2, except that the reaction temperature was increased from 180° C. to 280° C.

The reaction results are set forth in Table 1. Propylene was produced with good selectivity as shown in Table 1.

Example 5

Reaction was performed in the same manner as in Example 4, except that 0.6 g of the β-zeolite was replaced by 1.0 g of γ-alumina (N611N manufactured by JGC CORPORATION, compacted at 20 MPa and classified to 250 to 500 μm).

The reaction results are set forth in Table 1. Propylene was produced with good selectivity as shown in Table 1.

Example 7

(Production of Dehydration Catalyst)

$H_{0.5}K_{2.5}PW_{12}O_{40}$ (potassium phosphotungstate in which the hydrogen atoms in the phosphotungstic acid were partially exchanged with potassium) in an amount of 2.0 g was added to 15 ml of ethanol, and the mixture was stirred at 40° C. for 1 hour. Subsequently, 6.9 g of tetraethoxysilane was added thereto dropwise and the mixture was stirred at 40° C. for 1 hour. Further, 3.0 g of water was added thereto and the mixture was stirred at 80° C. for 24 hours. The resultant sol was evaporated to dryness, and the solid obtained was added to water at 80° C., followed by stirring for 15 hours. The solid was filtered, washed with water, dried and calcined at 300° C. to afford a dehydration catalyst in which $H_{0.5}K_{2.5}PW_{12}O_{40}$ was supported on silica in a weight ratio of 1:1.

TABLE 1

|  | Reaction time | Reaction temperature | Hydrogen/ acetone (molar ratio) | Acetone conversion (%) | Selectivity (%)/acetone | | Selectivity (%)/(acetone-IPA-DIPE) | | | |
|---|---|---|---|---|---|---|---|---|---|---|
|  |  |  |  |  | IPA (%) | DIPE (%) | Propylene | Propane | Propylene dimer | Others |
| Ex. 1 | 80 h | 180° C. | 6 | 99.9 | 7.3 | 1.4 | 92.2 | 5.9 | 1.9 | 0.0 |
| Ex. 2 | 80 h | 180° C. | 11 | 73.1 | 12.7 | 2.0 | 92.9 | 0.0 | 2.4 | 4.7 |
| Ex. 3 | 80 h | 240° C. | 11 | 90.3 | 1.3 | 0.6 | 91.6 | 0.0 | 1.6 | 6.8 |
| Ex. 4 | 80 h | 280° C. | 11 | 99.9 | 0.1 | 0.1 | 92.1 | 0.5 | 4.8 | 2.6 |
| Ex. 5 | 80 h | 280° C. | 11 | 99.8 | 0.3 | 0.7 | 83.6 | 0.6 | 9.6 | 6.2 |

IPA = isopropanol
DIPE = diisopropyl ether

Example 6

A fixed bed reaction apparatus was used which was equipped with a high-pressure feed pump, a high-pressure hydrogen mass flow controller, a high-pressure nitrogen mass flow controller, an electric furnace, a reactor having a catalyst-packing part, and a back pressure valve. A pressurized liquid-phase downflow reaction was carried out in the reaction apparatus.

The reactor was a SUS 316 reactor having an inner diameter of 1 cm. The 5% Ag-0.5% In/silica catalyst (classified to 250 to 500 μm) from Production Example 2 in an amount of 3.0 g was packed through the outlet of the reactor to form an upstream catalyst layer. Further, a mixture of 3.0 g of the hydrogenation catalyst and 1.0 g of tungsten oxide ($NO_3$) was packed to form a downstream catalyst layer.

The pressure was increased to 3.0 MPa with hydrogen. Under a stream of hydrogen at 22 ml/min, acetone was passed from the inlet side of the reactor at a rate of 0.30 g/h at 300° C.

Nitrogen was introduced at 50 ml/min in the middle between the reactor outlet and the back pressure valve through the high-pressure nitrogen mass flow controller. A gas chromatograph was located in the line downstream from the back pressure valve, and the reaction products were quantitatively determined online. The reaction results are set forth in Table 2. Propylene was produced with good selectivity as shown in Table 2.

(Reaction)

Reaction was performed in the same manner as in Example 6, except that the tungsten oxide ($WO_3$) was replaced by 1.0 g of the above dehydration catalyst (in which $H_{0.5}K_{2.5}PW_{12}O_{40}$ was supported on silica). The reaction results are set forth in Table 2. Propylene was produced with good selectivity as shown in Table 2.

Example 8

(Production of Dehydration Catalyst)

A dehydration catalyst in which $K_3PW_{12}O_{40}$ was supported on silica in a weight ratio of 1:1 was prepared in the same manner as in Example 7, except that $H_{0.5}K_{2.5}PW_{12}O_{40}$ (potassium phosphotungstate in which the hydrogen atoms in the phosphotungstic acid were partially exchanged with potassium) was replaced by $K_3PW_{12}O_{40}$ (potassium phosphotungstate in which all the hydrogen atoms in the phosphotungstic acid were exchanged with potassium).

(Reaction)

Reaction was performed in the same manner as in Example 6, except that the tungsten oxide ($WO_3$) was replaced by 1.0 g of the above dehydration catalyst (in which $K_3PW_{12}O_{40}$ was supported on silica). The reaction results are set forth in Table 2. Propylene was produced with good selectivity as shown in Table 2.

TABLE 2

| | Reaction time | Reaction temperature | Hydrogen/acetone (molar ratio) | Acetone conversion (%) | Selectivity (%)/acetone | | | | | |
|---|---|---|---|---|---|---|---|---|---|---|
| | | | | | IPA | DIPE | Propylene | Propane | Propylene dimer | Others |
| Ex. 6 | 100 h | 300° C. | 11 | 99.9 | 0.0 | 0.0 | 93.4 | 4.1 | 1.2 | 1.3 |
| Ex. 7 | 100 h | 300° C. | 11 | 99.9 | 0.0 | 0.0 | 97.5 | 0.5 | 1.7 | 0.3 |
| Ex. 8 | 100 h | 300° C. | 11 | 99.9 | 0.0 | 0.0 | 98.2 | 0.5 | 1.2 | 0.1 |

IPA = isopropanol
DIPE = diisopropyl ether

Example 9

(Production of Isopropyl Alcohol and Acetone)

Isopropyl alcohol was produced using isopropyl alcohol-producing *Escherichia coli* bacteria (*Escherichia coli* pGAP-Iaaa/B strain) described in Example 4 of WO 2009/008377. Here, a production apparatus 10 as illustrated in FIG. 1 of WO 2009/008377 was used. A culture tank, a trap tank, an injection tube, a connection tube and a discharge tube were all made of glass. The culture tank and the trap tank each had a capacity of 3 L. The trap tank contained 1.8 L of water as trap liquid (trap water). The trap water had been cooled to 10° C.

A waste tube was attached to the culture tank, and the increase of the culture liquid by the feed of sugars or neutralizers was controlled by appropriately discharging the culture liquid from the culture tank.

The pGAP-Iaaa/B strain was inoculated in a 100 mL conical flask that contained 25 mL of LB Broth, Miller culture liquid (Difco 244620) containing 50 μg/mL of ampicillin, and was pre-cultured overnight with stirring at 120 rpm and a culture temperature of 35° C. The whole amount of the culture liquid was transferred to the 3 L culture tank (fermentor BMS-PI manufactured by ABLE & Biott Co., Ltd.) that contained 1475 g of a culture medium having the composition below. The culture liquid was cultured with aeration at 1.5 L/min at atmospheric pressure, a stirring speed of 550 rpm, a culture temperature of 35° C. and pH of 7.0 (adjusted with an aqueous $NH_3$ solution). A 45 wt/wt % aqueous glucose solution was added at 7.5 g/L/h for 8 hours from the initiation of the culture. Afterward, the 45 wt/wt % aqueous glucose solution was added at 15 g/L/h. The trap water after 130 hours after the culture initiation was analyzed by GC and was found to contain 1.6 wt % of acetone and 5.6 wt % of isopropyl alcohol.

<Culture Medium Composition>

Corn steep liquor (NIHON SHOKUHIN KAKO CO., LTD.): 20 g/L $Fe_2SO_4.7H_2O$: 0.09 g/L $K_2HPO_4$: 2 g/L $KH_2PO_4$: 2 g/L $MgSO_4.7H_2O$: 2 g/L $(NH_4)_2SO_4$: 2 g/L ADEKA NOL LG126 (ADEKA CORPORATION): 0.6 g/L Water: balance Production of Propylene The aqueous solution containing isopropyl alcohol and acetone (the trap water after 130 hours from the culture initiation) was distilled to concentrate isopropyl alcohol and acetone.

In detail, 1947.0 g of the aqueous solution was passed at 500 mL/h through a column packed with 240 mL of a cation exchange resin (AMBERLYST 31WET manufactured by ORGANO CORPORATION), thereby removing residual ammonia. The treated liquid was distilled at normal pressure to separate fractions having a boiling point of 53 to 81.6° C. Gas chromatography showed that the fractions contained 22.6 wt % of acetone, 58.7 wt % of isopropyl alcohol and a balance of water.

Reaction was carried out in the same manner as in Example 8, except that acetone was replaced by the above mixture liquid containing isopropyl alcohol, acetone and water, and the amount of the $K_3PW_{12}O_{40}$-silica catalyst was increased from 1.0 g to 1.5 g. The reaction results are set forth in Table 3. Propylene was produced with good selectivity as shown in Table 3.

TABLE 3

| | Reaction time | Reaction temperature | Hydrogen/acetone (molar ratio) | Acetone conversion (%) | Selectivity (%)/(acetone + IPA) | | | | | |
|---|---|---|---|---|---|---|---|---|---|---|
| | | | | | IPA | DIPE | Propylene | Propane | Propylene dimer | Others |
| Ex. 9 | 100 h | 300° C. | 11 | 99.9 | 0.0 | 0.0 | 98.0 | 0.5 | 1.0 | 0.5 |

IPA = isopropanol
DIPE = diisopropyl ether

In Tables 1 to 3, the reaction time indicates the length of time from the initiation of the reaction after which the reaction results (acetone conversion, selectivity) were obtained. In detail, Table 1 shows that the reaction results were obtained after 80 hours after the initiation of the reaction, and Tables 2 and 3 show that the reaction results were determined after 100 hours after the initiation of the reaction.

Industrial Applicability

According to the present invention, a ketone and hydrogen are reacted directly in a single reaction step to yield an olefin with high selectivity. The processes of the invention thus provide industrial and practical advantages. By the processes of the invention, propylene can be obtained directly from acetone that is by-produced in the production of phenols by the cumene process.

The invention claimed is:

1. An olefin production process comprising reacting a ketone and hydrogen in the presence of at least one dehydration catalyst and an indium-silver-containing catalyst, the at least one dehydration catalyst being selected from metal oxide catalysts containing at least one Group 6 (VIB) element, zeolites, aluminas and heteropoly acid salts in which part or all the protons in heteropoly acids are exchanged with metal cations.

2. The olefin production process according to claim 1, wherein the dehydration catalyst is at least one dehydration catalyst selected from zeolites, γ-aluminas, tungsten oxide, molybdenum oxide and heteropoly acid salts in which part or all the protons in heteropoly acids are exchanged with metal cations.

3. The olefin production process according to claim 1, wherein the ketone is acetone and the olefin is propylene.

4. The olefin production process according to claim 1, wherein the heteropoly acid is at least one heteropoly acid selected from phosphotungstic acid, silicotungstic acid, phosphomolybdic acid and silicomolybdic acid.

5. The olefin production process according to claim 1, wherein the heteropoly acid salt is supported on silica.

6. The olefin production process according to claim 1, wherein the reaction temperature in the reaction is in the range of 50 to 500° C.

7. The olefin production process according to claim 1, wherein the reaction is catalyzed by a mixture of the dehydration catalyst and the indium-silver-containing catalyst.

8. The olefin production process according to claim 1, wherein the ketone is acetone obtained with an isopropyl alcohol-producing bacterium that produces isopropyl alcohol and acetone from a plant-derived material, and the olefin is propylene.

* * * * *